(12) United States Patent
Higuchi et al.

(10) Patent No.: US 9,921,180 B2
(45) Date of Patent: Mar. 20, 2018

(54) GAS SENSOR SYSTEM

(71) Applicant: NGK SPARK PLUG CO., LTD., Nagoya-shi, Aichi (JP)

(72) Inventors: Yuzo Higuchi, Komaki (JP); Tomonori Uemura, Komaki (JP)

(73) Assignee: NGK SPARK PLUG CO., LTD., Nagoya-shi, Aichi (JP)

(*) Notice: Subject to any disclaimer, the term of this patent is extended or adjusted under 35 U.S.C. 154(b) by 0 days.

(21) Appl. No.: 14/870,334

(22) Filed: Sep. 30, 2015

(65) Prior Publication Data

US 2016/0097738 A1 Apr. 7, 2016

(30) Foreign Application Priority Data

Oct. 1, 2014 (JP) .................................. 2014-203301

(51) Int. Cl.
*G01N 27/417* (2006.01)

(52) U.S. Cl.
CPC ................................ *G01N 27/4175* (2013.01)

(58) Field of Classification Search
CPC .......................................... G01N 27/406–27/41
See application file for complete search history.

(56) References Cited

U.S. PATENT DOCUMENTS

2007/0273540 A1* 11/2007 Inoue .................... G01N 27/407
                                                          340/632
2008/0060941 A1  3/2008 Ieda et al.
2012/0266647 A1 10/2012 Barnikow et al.

FOREIGN PATENT DOCUMENTS

JP    2008-070194 A    3/2008
JP    2008-233046 A   10/2008

OTHER PUBLICATIONS

Office Action ("Notification of Reasons for Refusal" dated Jan. 30, 2018 for corresponding Japanese Patent Application No. 2014-203301.

* cited by examiner

*Primary Examiner* — J. Christopher Ball
(74) *Attorney, Agent, or Firm* — Sughrue Mion, PLLC (57) ABSTRACT

A gas sensor system (1) includes a gas sensor (2) having a cell (14) electrically communicating with a first terminal T1 and a second terminal T2, and a cell (24) electrically communicating with T2 and a third terminal T3; and a sensor control section (40) including detection circuits (41, 43) for detecting the terminal potentials V1, V3. The sensor control section includes circuit (44) for bringing T2 to an examination potential Vex; constant current circuits (47, 48) for supplying examination currents Ipoc, Icp; terminal potential detection means S5 for detecting V1, V3 before the gas sensor detects the gas concentration in an activated state, and in a state in which T2 is brought to examination potential Vex and Ipoc, Icp are supplied to the cells (14, 24); and wire breakage determination means S6, S10 for determining a wire breakage anomaly and its location based on the V1, V3.

11 Claims, 6 Drawing Sheets

GAS SENSOR SYSTEM

BACKGROUND OF THE INVENTION

1. Field of the Invention

The present invention relates to a gas sensor system which includes a gas sensor having an oxygen pump cell and an oxygen concentration detection cell, and a sensor control section for controlling the gas sensor.

2. Description of the Related Art

Conventionally known gas sensors include a full-range air-fuel-ratio sensors having two cells (an oxygen pump cell and an oxygen concentration detection cell) and an NOx sensor having three cells (the above-described two cells and a cell for detecting the concentration of NOx gas). Such a gas sensor constitutes a gas sensor system in cooperation with a sensor control section for controlling the gas sensor, and the gas sensor system is mounted on a vehicle or the like.

Incidentally, such a gas sensor system may suffer a wire breakage anomaly in which one of the wiring lines of the gas sensor connected to the sensor control section is broken. In view of this, heretofore, a gas sensor system which can perform self-diagnosis of such a wire breakage anomaly has been proposed.

For example, Patent Document 1 discloses a sensor control apparatus for an NOx sensor having three cells, which control apparatus includes wire breakage determination means for determining whether or not a wire breakage has occurred based on a change in the detected pump current with a change in reference voltage applied to the second oxygen pump cell.

[Patent Document 1] Japanese Patent Application Laid-Open (kokai) No. 2008-233046

3. Problem to be Solved by the Invention

However, in the conventional wire breakage anomaly diagnosis method disclosed in Patent Document 1, a response of the pump current flowing through the oxygen pump cell is detected after the gas sensor is activated. Therefore, the method cannot diagnose wire breakage anomaly (specifically, whether or not a wire breakage has occurred and the location of the wire breakage) until the gas sensor is activated.

SUMMARY OF THE INVENTION

The present invention has been made to address the above problem, and an object thereof is to provide a gas sensor system which can properly determine, through diagnosis, whether or not a gas sensor has a wire breakage anomaly and the location of the wire breakage anomaly before the gas sensor performs gas detection in an activated state.

In a first embodiment (1), the invention provides a gas sensor system comprising a gas sensor having an oxygen pump cell electrically communicating with a first terminal and a second terminal, and an oxygen concentration detection cell electrically communicating with the second terminal and a third terminal, the gas sensor detecting the concentration of a specific gas contained in a gas under measurement; and a sensor control section which includes a first terminal potential detection circuit for detecting a first terminal potential of the first terminal and a third terminal potential detection circuit for detecting a third terminal potential of the third terminal and which controls the gas sensor through the first terminal, the second terminal, and the third terminal. The sensor control section includes an examination potential circuit which brings the second terminal to a predetermined examination potential; a first constant current circuit which supplies a predetermined first examination current to the oxygen pump cell through the first terminal; a second constant current circuit which supplies a predetermined second examination current to the oxygen concentration detection cell through the third terminal; terminal potential detection means for detecting the first terminal potential and the third terminal potential using the first terminal potential detection circuit and the third terminal potential detection circuit, before the gas sensor detects in an activated state the concentration of the specific gas contained in the gas under measurement, and in a state in which the second terminal is brought to the examination potential by the examination potential circuit, the first examination current is supplied from the first constant current circuit to the oxygen pump cell through the first terminal, and the second examination current is supplied from the second constant current circuit to the oxygen concentration detection cell through the third terminal; and wire breakage diagnosis means for determining whether or not the gas sensor has a wire breakage anomaly and a location where the wire breakage anomaly has occurred based on the detected first terminal potential and the detected third terminal potential.

In this gas sensor system, before the gas sensor detects the concentration of the specific gas contained in the gas under measurement in the activated state (specifically, not only during activation but also before the gas sensor already activated detects the gas concentration), the second terminal is brought to the examination potential, the first examination current is supplied to the oxygen pump cell through the first terminal, and the second examination current is supplied to the oxygen concentration detection cell through the third terminal. The first terminal potential and the third terminal potential are then detected.

As a result of this operation, not only in the case where the gas sensor has already been activated but also in the middle of activation, once the oxygen pump cell and the oxygen concentration detection cell exhibit oxygen ion conductivity and a lower internal resistance, the first terminal potential and the third terminal potential assume different values depending on whether or not the wiring lines connected to the terminals are broken.

The first terminal potential and the third terminal potential in both cases where no wire breakage has occurred and where wire breakage has occurred will be described specifically.

In the case where none of the wiring lines has a wire breakage anomaly, when the first examination current and the second examination current are supplied, the first terminal potential and the third terminal potential theoretically become equal to potentials obtained by adding to the examination potential the voltage drops generated due to the internal resistance of both the oxygen pump cell and the oxygen concentration detection cell and the electromotive force of the respective oxygen concentrations cells. However, in the case where the oxygen pump cell and the oxygen concentration detection cell do not exhibit oxygen ion conductivity or in the case where the internal resistance of the oxygen pump cell and the oxygen concentration detection cell are high even though they exhibit oxygen ion conductivity, the first terminal potential and the third terminal potential are limited by the maximum output voltages of the first constant current circuit and the second constant current circuit.

Meanwhile, when the temperature of the oxygen pump cell and the oxygen concentration detection cell rise, the oxygen pump cell and the oxygen concentration detection cell exhibit oxygen ion conductivity and a lower internal resistance, the first terminal potential and the third terminal potential become lower than the maximum output voltages of the first constant current circuit and the second constant current circuit, and become equal to the theoretical potentials obtained by adding to the examination potential the voltage drops due to the internal resistance and electromotive force of the respective oxygen concentration cells.

In contrast, in the case where one of the wiring lines is broken, since the first examination current or the second examination current does not flow, the first constant current circuit or the second constant current circuit continues to output the maximum output voltage, and at least one of the first terminal potential and the third terminal potential remains the same as the maximum output voltage.

In view of the above, in this gas sensor system, the first terminal potential and the third terminal potential are detected in the above-described state, and, based on these potentials, the presence/absence of a wire breakage anomaly and the location of wire breakage anomaly are determined for the first terminal, the second terminal, and the third terminal.

As a result, the presence/absence of a wire breakage anomaly and the location of wire breakage anomaly can be determined properly through diagnosis, not only once the gas sensor is activated but also during activation of the gas sensor.

Notably, in the case where the gas sensor in a low temperature state (inactivated state) is heated and activated, the diagnosis of wire breakage anomaly becomes possible while heating when the oxygen pump cell and the oxygen concentration detection cell exhibit oxygen ion conductivity and a lower internal resistance as described above. In other words, a wire breakage anomaly cannot be diagnosed properly before that time. Therefore, it is necessary to wait until the gas sensor is heated to a temperature at which the diagnosis of wire breakage anomaly can be performed.

Therefore, examples of the timing for performing the diagnosis of a wire breakage anomaly include a timing which is after the detected temperature of the gas sensor becomes equal to or higher than a predetermined temperature and a timing which is after a predetermined time has elapsed after the start of heating the gas sensor.

Also, the detection of the first terminal potential and the third terminal potential may begin before the diagnosis of a wire breakage anomaly becomes possible, and in the case where both the first terminal potential and the third terminal potential become lower than the maximum output voltage, the system may determine that no wire breakage is present. Notably, in the case where at least one of the first terminal potential and the third terminal potential remains the same as the maximum output voltage even after elapse of the predetermined time, the system determines that a wire breakage is present. In the case where the system has such a configuration, when a wire breakage anomaly is absent, the system can determine that no wire breakage anomaly is present before the predetermined time has elapsed.

Meanwhile, in the case where the gas sensor is already in the activated state immediately after startup of the system; for example, in the case of a hot restart, the system can perform the diagnosis of a wire breakage anomaly without waiting.

In a preferred embodiment (2) of the above-described gas sensor system (1), the wire breakage diagnosis means determines, based on the first terminal potential and the third terminal potential, a wire breakage absence state in which none of a first wiring line connecting the oxygen pump cell to the first terminal, a second wiring line connecting the oxygen pump cell and the oxygen concentration detection cell to the second terminal, and a third wiring line connecting the oxygen concentration detection cell to the third terminal is broken, a first wire breakage state in which the first wiring line is broken, a second wire breakage state in which the second wiring line is broken, and a third wire breakage state in which the third wiring line is broken.

In this gas sensor system, the wire breakage diagnosis means determines the wire breakage absence state and the three wire breakage states based on the first terminal potential and the third terminal potential. Therefore, when a wire breakage anomaly occurs, its location can be properly determined and reported to an external device such as an ECU.

In another preferred embodiment (3) of the above-described gas sensor system (2), the wire breakage diagnosis means includes wire breakage absence determination means which determines that the gas sensor is in the wire breakage absence state when the first terminal potential falls within a first range ranging from the examination potential to a first threshold potential lower than a maximum output voltage of the first constant current circuit, and the third terminal potential falls within a second range ranging from the examination potential to a second threshold potential lower than a maximum output voltage of the second constant current circuit.

In this gas sensor system, the wire breakage absence determination means of the wire breakage diagnosis means determines that the gas sensor is in the wire breakage absence state in which no wiring line is broken when the first terminal potential falls within the first range and the third terminal potential falls within the second range. In this manner, it is possible to properly determine whether or not the gas sensor is in the wire breakage absence state. The determination method is described as follows.

When as a result of heating of the gas sensor, the oxygen pump cell and the oxygen concentration detection cell exhibit oxygen ion conductivity and a lower internal resistance, the first terminal potential becomes lower than the maximum output voltage of the first constant current circuit if the gas sensor is in the wire breakage absence state. Specifically, the first terminal potential becomes equal to a potential obtained by adding to the examination potential the voltage drop due to the internal resistance of the oxygen pump cell and the electromotive force of the oxygen concentration cell. Similarly, if the gas sensor is in the wire breakage absence state, the third terminal potential becomes lower than the maximum output voltage of the second constant current circuit. Specifically, the third terminal potential becomes equal to a potential obtained by adding to the examination potential the voltage drop due to the internal resistance of the oxygen concentration detection cell and the electromotive force of the oxygen concentration cell.

Therefore, in the case where the first terminal potential falls within the first range (ranging from the examination potential to the first threshold potential lower than the maximum output voltage of the first constant current circuit) and the third terminal potential falls within the second range (ranging from the examination potential to the second threshold potential lower than the maximum output voltage of the second constant current circuit), the gas sensor is determined to be in the wire breakage absence state in which none of the wiring lines connected to the first terminal, the second terminal, and the third terminal is broken.

Notably, in the case where the first examination current and the second examination current are supplied to the oxygen pump cell and the oxygen concentration detection cell in a state in which the temperature of the oxygen pump cell and the oxygen concentration detection cell are low and their internal resistance is still high (for example, several hundreds kΩ or higher), an excessively high voltage is applied between opposite ends of each cell, and so called blackening (the phenomenon in which each cell is blackened) may possibly occur. Therefore, preferably, the first examination current and the second examination current are a small current of, for example, about 10 to 20 µA.

In yet another preferred embodiment (4) of the above-described gas sensor system (3), the wire breakage diagnosis means includes wire breakage state determination means, operable when the wire breakage absence determination means determines that the gas sensor is not in the wire breakage absence state, for determining based on the first terminal potential and the third terminal potential, whether the gas sensor is in the first wire breakage state, the second wire breakage state, or the third wire breakage state.

In this gas sensor system, when the wire breakage absence determination means determines that the gas sensor is not in the wire breakage absence state (namely, when the gas sensor has a wire breakage anomaly), the wire breakage state determination means determines whether the gas sensor is in the first wire breakage state, the second wire breakage state, or the third wire breakage state (the location of the wire breakage anomaly).

In yet another preferred embodiment (5) of the above-described gas sensor system (4), the wire breakage state determination means determines that the gas sensor is in the first wire breakage state when the third terminal potential falls within the second range and the first terminal potential is higher than the first range, the wire breakage state determination means determines that the gas sensor is in the second wire breakage state when the first terminal potential is higher than the first range and the third terminal potential is higher than the second range, and the wire breakage state determination means determines that the gas sensor is in the third wire breakage state when the first terminal potential falls within the first range and the third terminal potential is higher than the second range.

In this gas sensor system, the wire breakage state determination means can properly determine the three wire breakage states based on the first terminal potential and the third terminal potential.

Notably, the specific method of determining a wire breakage anomaly by the wire breakage state determination means is as follows.

First, the case is considered where although the second wiring line connected to the second terminal and the third wiring line connected to the third terminal are normal, the first wiring line connected to the first terminal is broken (the first wire breakage state).

In this case, the first examination current does not flow to the oxygen pump cell, and the first constant current circuit keeps outputting the maximum output voltage, for example, a voltage approximately equal to the power supply voltage of the sensor control section. The maximum output voltage is detected as the first terminal potential.

Meanwhile, when the oxygen concentration detection cell exhibits oxygen ion conductivity and a lower internal resistance, the third terminal potential becomes equal to a potential (a potential within the second range) which is lower than the maximum output voltage of the second constant current circuit and which is obtained by adding to the examination potential the voltage drop due to the internal resistance of the oxygen concentration detection cell and the electromotive force of the oxygen concentration cell.

Accordingly, in the case where the third terminal potential falls within the second range and the first terminal potential is higher than the first range, the gas sensor is determined to be in the first wire breakage state.

Next, the case is considered where although the first wiring line connected to the first terminal and the second wiring line connected to the second terminal are normal, the third wiring line connected to the third terminal is broken (the third wire breakage state).

In this case, the second examination current does not flow to the oxygen concentration detection cell, and the second constant current circuit keeps outputting the maximum output voltage, for example, a voltage approximately equal to the power supply voltage of the sensor control section. The maximum output voltage is detected as the third terminal potential. Meanwhile, when the oxygen pump cell exhibits oxygen ion conductivity and a lower internal resistance, the first terminal potential becomes equal to a potential (a potential within the first range) which is lower than the maximum output voltage of the first constant current circuit and which is obtained by adding to the examination potential the voltage drop due to the internal resistance of the oxygen pump cell and the electromotive force of the oxygen concentration cell.

Accordingly, in the case where the first terminal potential falls within the first range and the third terminal potential is higher than the second range, the gas sensor is determined to be in the third wire breakage state.

Further, the case is considered where although the first wiring line connected to the first terminal and the third wiring line connected to the third terminal are normal, and the second wiring line connected to the second terminal is broken (the second wire breakage state).

In this case, the second wiring line is broken and the ends of the oxygen pump cell and the oxygen concentration detection cell which were connected to the second terminal are not fixed to the examination potential. Therefore, when an attempt is made to supply the first examination current and the second examination current, both the first constant current circuit and the second constant current circuit continue to output their maximum output voltages. These maximum output voltages are detected as the first terminal potential and the third terminal potential.

Accordingly, in the case where the first terminal potential is higher than the first range and the third terminal potential is higher than the second range in a state in which the oxygen pump cell and the oxygen concentration detection cell exhibit oxygen ion conductivity and a lower internal resistance, the second wiring line connected to the second terminal is determined to be broken.

In yet another preferred embodiment (6) of any of the above-described gas sensor systems (1) to (5), the gas sensor internally has a measurement chamber into which the gas under measurement is introduced and a reference oxygen chamber in which a reference oxygen atmosphere is generated; the oxygen concentration detection cell has a first detection electrode facing the reference oxygen chamber and electrically communicating with the third terminal and a second detection electrode exposed to the measurement chamber and electrically communicating with the second terminal; and the second constant current circuit comprises a constant current output circuit which supplies a constant current to the oxygen concentration detection cell through the third terminal so as to pump oxygen into the reference oxygen chamber.

In this gas sensor system, the second constant current comprises a constant current output circuit. Therefore, when the diagnosis of wire breakage anomaly is performed, the constant current output circuit outputs the second examination current. Accordingly, it is unnecessary to provide a dedicated circuit for supplying the second examination current. Notably, the configuration of the constant current output circuit can be simplified by rendering the magnitude of the second examination current equal to the magnitude of the constant current for pumping oxygen into the reference oxygen chamber (the second examination current=the constant current).

In yet another preferred embodiment (7) of the above-described gas sensor system (6), the sensor control section includes a detection cell current switch for turning on and turning off supply of the second examination current and the constant current from the constant current output circuit to the oxygen concentration detection cell through the third terminal, and first cutoff means for turning off the detection cell current switch when the wire breakage diagnosis means determines that a wire breakage anomaly is present.

In this gas sensor system, when the system determines that a wire breakage anomaly is present, the system cuts off the second examination current and the constant current. Therefore, it is possible to prevent blackening of the oxygen concentration detection cell, which would otherwise occur when the second examination current or the constant current is supplied in a state in which the wire breakage anomaly continues.

In yet another preferred embodiment (8) of any of the above-described gas sensor systems (1) to (7), the gas sensor internally has a measurement chamber into which the gas under measurement is introduced; the oxygen pump cell has a first pump electrode disposed outside the measurement chamber and electrically communicating with the first terminal and a second pump electrode exposed to the measurement chamber and electrically communicating with the second terminal; and the first constant current circuit comprises a pump current output circuit which supplies a pump current to the oxygen pump cell through the first terminal so as to pump oxygen out of the measurement chamber or pump oxygen into the measurement chamber.

In this gas sensor system, the first constant current circuit comprises a pump current output circuit. Therefore, when diagnosis of wire breakage anomaly is performed, the pump current output circuit outputs the predetermined first examination current instead of the pump current. Accordingly, it is unnecessary to provide a dedicated circuit for supplying the first examination current.

In yet another preferred embodiment (9) of the above-described gas sensor system (8), the sensor control section includes a pump current switch for turning on and turning off supply of the first examination current and the pump current from the pump current output circuit to the oxygen pump cell through the first terminal, and second cutoff means for turning off the pump current switch when the wire breakage diagnosis means determines that a wire breakage anomaly is present.

In this gas sensor system, when the system determines that a wire breakage anomaly is present, the system cuts off the first examination current and the pump current. Therefore, it is possible to prevent blackening of the oxygen pump cell, which would otherwise occur when the first examination current or the pump current is supplied in a state in which the wire breakage anomaly continues.

In yet another preferred embodiment (10) of any of the above-described gas sensor systems (1) to (9), the examination potential circuit comprises a reference potential circuit which applies a reference potential to the second terminal after the gas sensor is activated.

In this gas sensor system, the examination potential circuit comprises reference potential circuit which applies the reference potential after the gas sensor is activated. Therefore, it is unnecessary to provide a dedicated examination potential circuit for the diagnosis of wire breakage anomaly.

In yet another preferred embodiment (11) of the above-described gas sensor system (10), the sensor control section includes a reference potential switch for turning on and turning off application of the examination potential and the reference potential from the reference potential circuit to the second terminal, and third cutoff means for turning off the reference potential switch when the wire breakage diagnosis means determines that a wire breakage anomaly is present.

In this gas sensor system, when the system determines that a wire breakage anomaly is present, the system discontinues application of the examination potential and the reference potential. Therefore, it is possible to prevent blackening of the oxygen pump cell and the oxygen concentration detection cell, which would otherwise occur when the examination potential or the reference potential is applied in a state in which the wire breakage anomaly continues.

DESCRIPTION OF SYMBOLS

Reference numerals and symbols, used to identify various features in the drawings include the following.
ENG: internal combustion engine (engine)
EP: exhaust pipe
EG: exhaust gas (gas under measurement)
100: ECU
1: gas sensor system
2: gas sensor
3: sensor element section 14: oxygen pump cell
12: first pump electrode
16: second pump electrode
24: oxygen concentration detection cell
28: first detection electrode
22: second detection electrode
20: measurement chamber
26: reference oxygen chamber
80: heater section
Ip: pump current
Ipoc: first examination current
Icp: second examination current, minute current (constant current)
T1: first terminal
T2: second terminal
T3: third terminal
L1: first wiring line
L2: second wiring line
L3: third wiring line
V1: first terminal potential
V2: second terminal potential
V3: third terminal potential
Vref: reference potential
Vex: examination potential
30: digital signal processor
40: sensor control section
41: A/D converter (first terminal potential detection circuit)
42: A/D converter
43: A/D converter (third terminal potential detection circuit)
44: operational amplifier (examination potential circuit, reference potential circuit)
45: first circuit
R1: first resistor
SW1: first switch
46: second circuit
R2: second resistor
SW2: second switch
47: D/A converter (first constant current circuit, pump current output circuit)
48: D/A converter (second constant current circuit, constant current output circuit)
SW3: third switch (pump current switch)
SW4: fourth switch (examination potential switch, reference potential switch)
SW5: fifth switch (detection cell current switch)
S5: terminal potential detection means
S6, S7: wire breakage absence determination means (wire breakage diagnosis means)
S10: wire breakage state determination means (wire breakage diagnosis means)
S8: first cutoff means, second cutoff means, third cutoff means

DETAILED DESCRIPTION OF THE PREFERRED EMBODIMENTS

The present invention will next be described in detail with reference to the drawings. However, the present invention should not be construed as being limited thereto.

Figure 1:
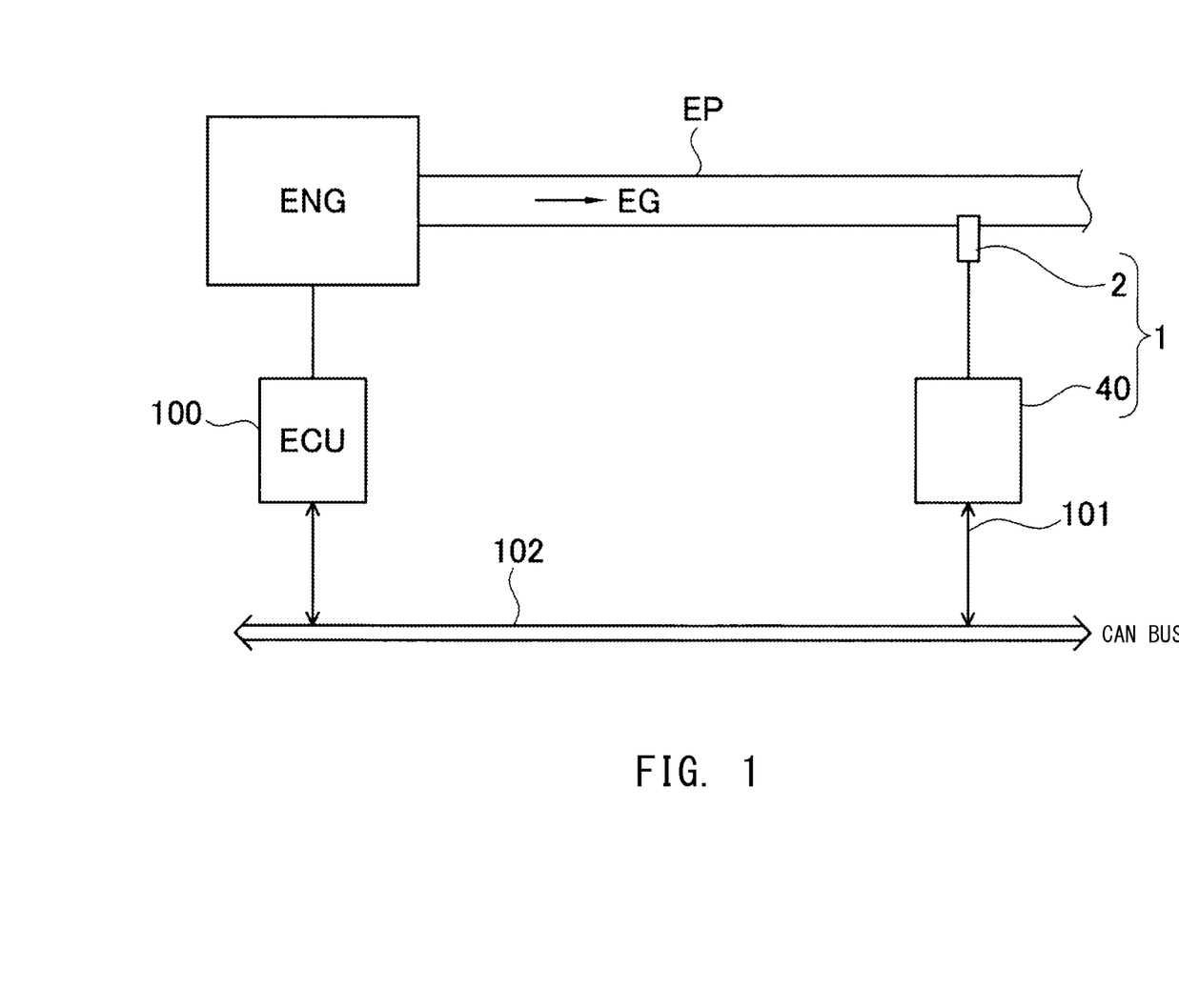
FIG. 1 is an explanatory diagram showing the overall configuration of an engine system in which a gas sensor system according to an embodiment is used for control of an internal combustion engine of a vehicle.
Figure 2:
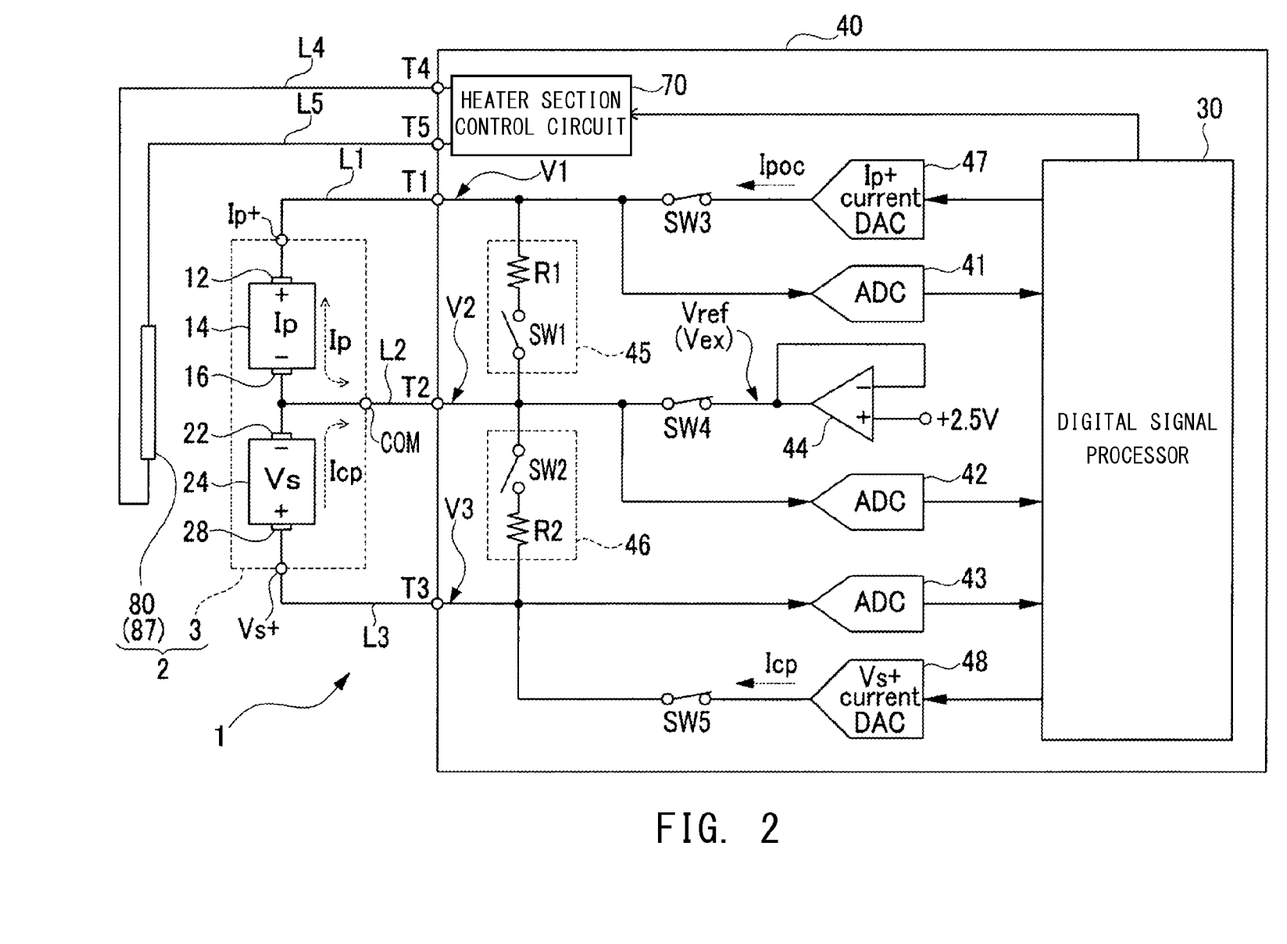
FIG. 2 is an explanatory diagram schematically showing the configuration of the gas sensor system according to the embodiment.

FIG. 1 is a diagram showing the overall configuration of an engine system in which a gas sensor system 1 according to the present embodiment is used for control of an internal combustion engine of a vehicle. FIG. 2 is a diagram schematically showing the configuration of the gas sensor system 1.

This gas sensor system 1 includes a gas sensor 2 attached to an exhaust pipe EP of an internal combustion engine ENG (engine) of a vehicle (not shown), and a sensor control section 40 for controlling the gas sensor 2.

Notably, the gas sensor 2 is an air-fuel-ratio sensor (full-range air-fuel-ratio sensor) which linearly detects the concentration of oxygen (the concentration of a specific gas) (air-fuel ratio) within exhaust gas EG (gas under measurement). The detected oxygen concentration (air-fuel ratio) is used for air-fuel-ratio feedback control of the internal combustion engine. As shown in FIG. 2, this gas sensor 2 has a sensor element section 3 for detecting the oxygen concentration and a heater section 80 for heating the sensor element section 3.

The sensor control section 40 is connected to the gas sensor 2 and controls the same. The gas sensor system 1 is connected to a CAN bus 102 of the vehicle through a connection bus 101, and can exchange data with an ECU 100 through transmission and reception of data. The sensor control section 40 is composed of an ASIC (Application Specific IC), and includes a digital signal processor 30, and a heater section control circuit 70 for controlling the heater section 80 as well as a circuit for controlling the sensor element section 3 of the gas sensor 2.

Figure 3:
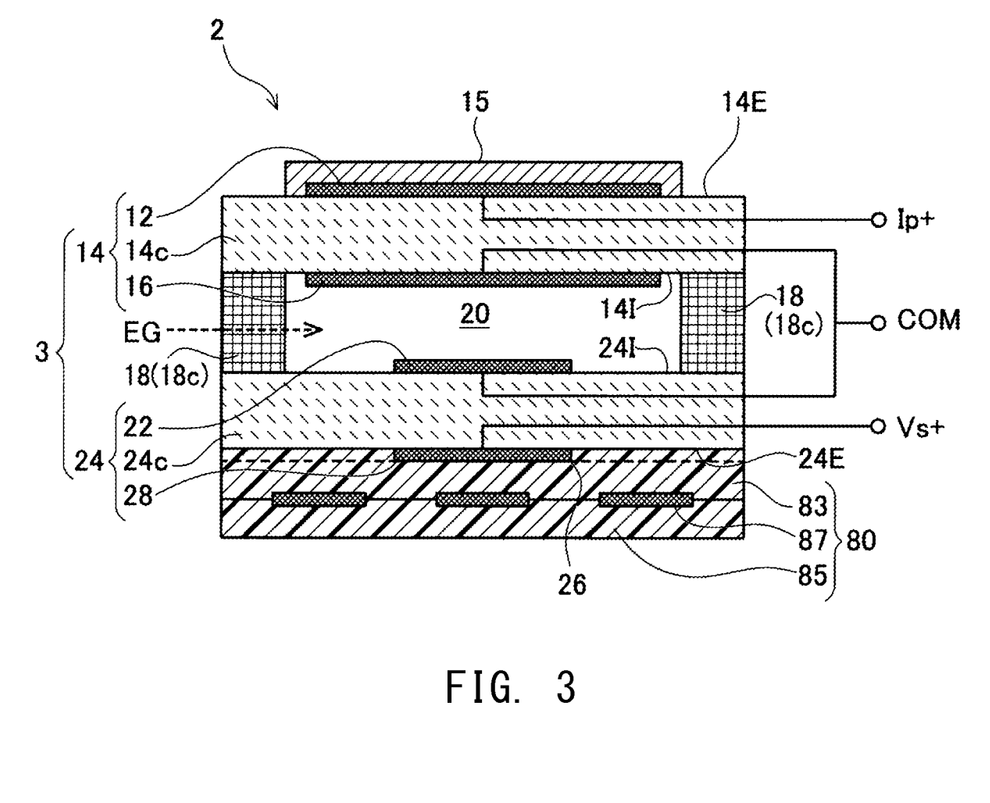
FIG. 3 is a schematic cross-sectional view of a gas sensor of the gas sensor system according to the embodiment.

First, the gas sensor 2 will be described. FIG. 3 is a schematic view showing the structure of the gas sensor 2. The sensor element section 3 of the gas sensor 2 is a laminate obtained by stacking an oxygen pump cell 14, a porous layer 18, and an oxygen concentration detection cell 24 in this order. The heater section 80 is stacked on the sensor element section 3.

The oxygen pump cell 14 has, as a substrate, an electrolyte layer 14c (a plate-shaped solid electrolyte member mainly made of zirconia and having oxygen ion conductivity), and a pair of electrodes 12 and 16 (porous electrodes) mainly made of porous platinum are formed on opposing surfaces of the electrolyte layer 14c. Specifically, the first pump electrode 12 is formed on an outer surface 14E of the electrolyte layer 14c which is one surface (located on the upper side in FIG. 3) of the electrolyte layer 14c, and the second pump electrode 16 is formed on an inner surface 141 of the electrolyte layer 14c which is the other (opposing) surface (located on the lower side in FIG. 3) of the electrolyte layer 14c.

Similarly, the oxygen concentration detection cell 24 has, as a substrate, an electrolyte layer 24c (a plate-shaped solid electrolyte member mainly made of zirconia and having oxygen ion conductivity), and a pair of electrodes 22 and 28 (porous electrodes) mainly made of porous platinum are formed on opposite surfaces of the electrolyte layer 24c. Specifically, the first detection electrode 28 is formed on an outer surface 24E of the electrolyte layer 24c which is one surface (located on the lower side in FIG. 3) of the electrolyte layer 24c, and the second detection electrode 22 is formed on an inner surface 241 of the electrolyte layer 24c which is the other (opposing) surface (located on the upper side in FIG. 3) of the electrolyte layer 24c.

The inner surface 141 of the electrolyte layer 14c of the oxygen pump cell 14 faces the inner surface 241 of the electrolyte layer 24c of the oxygen concentration detection cell 24, and the porous layer 18 is sandwiched between the electrolyte layer 14c and the electrolyte layer 24c. The porous layer 18 has porous wall portions 18c extending along the edges of the inner surface 141 of the electrolyte layer 14c and the inner surface 241 of the electrolyte layer 24c. The internal space of the porous layer 18 surrounded by the porous wall portions 18c, the electrolyte layer 14c, and the electrolyte layer 24c serves as a hollow measurement chamber 20 into which the exhaust gas EG can be introduced. Notably, the porous layer 18 allows the exhaust gas EG to flow into the measurement chamber 20, and restricts the inflow speed of the exhaust gas EG.

The second pump electrode 16 of the oxygen pump cell 14 and the second detection electrode 22 of the oxygen concentration detection cell 24 are exposed to the atmosphere within the measurement chamber 20. The electrodes 16 and 22 are electrically connected to each other and to a COM terminal of the sensor element section 3. The first pump electrode 12 of the oxygen pump cell 14 is connected to an Ip+ terminal of the sensor element section 3, and the first detection electrode 28 of the oxygen concentration detection cell 24 is connected to a Vs+ terminal of the sensor element section 3.

The entirety of the first pump electrode 12 of the oxygen pump cell 14 is covered with a protection layer 15 in order to suppress poisoning of the first pump electrode 12. The protection layer 15 is formed of porous ceramic or the like and is disposed in a flow path through which the exhaust gas EG flows. The exhaust gas EG can reach the first pump electrode 12 through the protection layer 15.

The heater section 80 is stacked on the outer surface 24E of the electrolyte layer 24c of the oxygen concentration detection cell 24, and has a structure in which a heater resistor 87 formed of conductor is sandwiched between a pair of alumina sheets 83 and 85. By raising the temperature of the sensor element section 3 by the heater section 80, the electrolyte layers 14c and 24c of the sensor element section 3 are activated. As a result, oxygen ions can move within the electrolyte layers 14c and 24c.

Also, the alumina sheet 83 of the heater section 80 covers the entirety of the first detection electrode 28 of the oxygen concentration detection cell 24 to thereby seal the first detection electrode 28. Notably, a space (hole) inside the first detection electrode 28 (porous electrode) constitutes a reference oxygen chamber 26, and functions as an internal oxygen reference source as described below.

Next, the gas sensor system 1 will be described with reference to FIG. 2. As described above, the sensor control section 40 is constituted by an ASIC including the digital signal processor 30 (hereinafter also referred to as the "processor 30"). This sensor control section 40 has a first terminal T1, a second terminal T2, and a third terminal T3, and controls the sensor element section 3 of the gas sensor 2 through these terminals. Notably, the first terminal T1 is connected to the Ip+ terminal of the sensor element section 3 through a first wiring line L1. The second terminal T2 is connected to the COM terminal of the sensor element section 3 through a second wiring line L2. The third terminal T3 is connected to the Vs+ terminal of the sensor element section 3 through a third wiring line L3.

The sensor control section 40 has A/D converters 41, 42, and 43 connected to the first terminal T1, the second terminal T2, and the third terminal T3, respectively.

The A/D converter 41 detects a first terminal potential V1 of the first terminal T1, converts it to a digital signal through A/D conversion, and inputs the digital signal to the processor 30. Similarly, the A/D converter 42 detects a second terminal potential V2 of the second terminal T2, converts it to a digital signal through A/D conversion, and inputs the digital signal to the processor 30. Similarly, the A/D converter 43 detects a third terminal potential V3 of the third terminal T3, converts it to a digital signal through A/D conversion, and inputs the digital signal to the processor 30.

Notably, the A/D converters 41, 42, and 43 are used for PID (proportional-integral-derivative) control of pump current Ip described below, and are also used when a wire breakage anomaly and short circuit anomaly of the gas sensor 2 are diagnosed as described below.

A first circuit 45 including a first resistor R1 and a first switch SW1 is connected between the first terminal T1 and the second terminal T2. The resistance R1$r$ of the first resistor R1 is 1 kΩ. The first switch SW1 establishes the connection between the first terminal T1 and the second terminal T2 through the first resistor R1, and brakes the connection.

Further, a second circuit 46 including a second resistor R2 and a second switch SW2 is connected between the second terminal T2 and the third terminal T3. The resistance of the second resistor R2 is 1 kΩ. The second switch SW2 connects the second terminal T2 and the third terminal T3 through the second resistor R2, and brakes the connection.

The first circuit 45 and the second circuit 46 are used for diagnosing a short circuit anomaly of the gas sensor 2. When a short circuit anomaly of the gas sensor 2 is diagnosed, the first switch SW1 and the second switch SW2 are turned on. Meanwhile, at the time of diagnosis of a wire breakage anomaly of the gas sensor 2 and at the time of ordinary use of the gas sensor 2, the first switch SW1 and the second switch SW2 are turned off. Notably, the diagnosis of a short circuit anomaly performed through use of the first circuit 45 and the second circuit 46 will not be described herein.

The output of a D/A converter (hereinafter referred to as a "current DAC") 47 is connected to the first terminal T1 through a third switch SW3. The current DAC 47 supplies the pump current Ip to the oxygen pump cell 14 in accordance with an instruction from the processor 30. The third switch SW3 allows the pump current Ip from the current DAC 47 to flow to the oxygen pump cell 14 through the first terminal T1 and cuts off the flow of the pump current Ip.

The output of an operational amplifier 44 is connected to the second terminal T2 through a fourth switch SW4. The operational amplifier 44 serves as a reference potential circuit which outputs a reference potential Vref of +2.5 V. The fourth switch SW4 allows and cuts off the application of the reference potential Vref from the operational amplifier 44 to the second terminal T2.

The output of a D/A converter (current DAC) 48 is connected to the third terminal T3 through a fifth switch SW5. The current DAC 48 supplies a constant minute current Icp (=20 μA) or current for detecting internal resistance to the oxygen concentration detection cell 24 in accordance with an instruction from the processor 30. The fifth switch SW5 allows the minute current Icp, etc., from the current DAC 48 to flow to the oxygen concentration detection cell 24 through the third terminal T3 and cuts off the flow of the minute current Icp, etc.

Notably, although the third switch SW3 through the fifth switch SW5 are turned on during ordinary use of the gas sensor 2 and during diagnosis of a wire breakage anomaly of the gas sensor 2, the third switch SW3 through the fifth switches SW5 are turned off after their initial setting or when a short circuit anomaly or wire breakage anomaly of the gas sensor 2 is detected.

The minute current Icp supplied to the oxygen concentration detection cell 24 forces the oxygen concentration detection cell 24 to pump oxygen within the measurement chamber 20 to the first detection electrode 28 (porous electrode). As a result, the reference oxygen chamber 26 functions as an internal oxygen reference source.

While supplying such a fixed minute current Icp to the oxygen concentration detection cell 24, the processor 30 performs so-called digital PID control; i.e., controls the pump current Ip supplied to the oxygen pump cell 14 such that a detection cell voltage Vs generated between the opposite ends of the oxygen concentration detection cell 24 (the difference between the third terminal potential V3 detected by the A/D converter 43 and the second terminal potential V2 detected by the A/D converter 42) becomes a predetermined voltage. As a result, oxygen contained in the exhaust gas EG introduced into the measurement chamber 20 through the porous layer 18 is pumped out and pumped into the measurement chamber 20.

The magnitude and direction of the pump current Ip supplied to the oxygen pump cell 14 and controlled by PID control of the processor 30 change depending on the concentration of oxygen (air-fuel ratio) in the exhaust gas EG introduced into the measurement chamber 20 through the porous layer 18. As a result, the concentration of oxygen in the exhaust gas EG can be detected based on the pump current Ip. Namely, the sensor control section 40 drives and controls the gas sensor 2 by feedback-controlling the pump current Ip supplied to the oxygen pump cell 14 such that the detection cell voltage Vs generated at the oxygen concentration detection cell 24 becomes a predetermined voltage.

Also, the sensor control section 40 has a fourth terminal T4 and a fifth terminal T5 connected to the heater section control circuit 70. These fourth and fifth terminals T4 and T5 are connected to the heater section 80 of the gas sensor 2 through a fourth wiring line L4 and a fifth wiring line L5. The heater section control circuit 70 is connected to the processor 30, and the supply of electric current to the heater section 80 is controlled through PWM (pulse-width-modulation) control in accordance with an instruction from the processor 30.

Notably, the details of the digital PID control of the pump current Ip and the PWM control of the heater section 80 performed by the processor 30 are well known to those of ordinary skill in the art and will not be described herein.

Notably, this gas sensor system 1 diagnoses a short circuit anomaly of the gas sensor 2 before heating the gas sensor 2 by the heater section 80. In the case where no short circuit anomaly is present, the gas sensor system 1 starts the supply of electric current to the heater section 80 so as to raise the temperature of the gas sensor 2, and performs the diagnosis of a wire breakage anomaly of the gas sensor 2 during activation of the gas sensor 2. Namely, the gas sensor system 1 diagnoses a wire breakage anomaly before the gas sensor 2 detects the oxygen concentration of the exhaust gas EG in an activated state.

Figure 4:
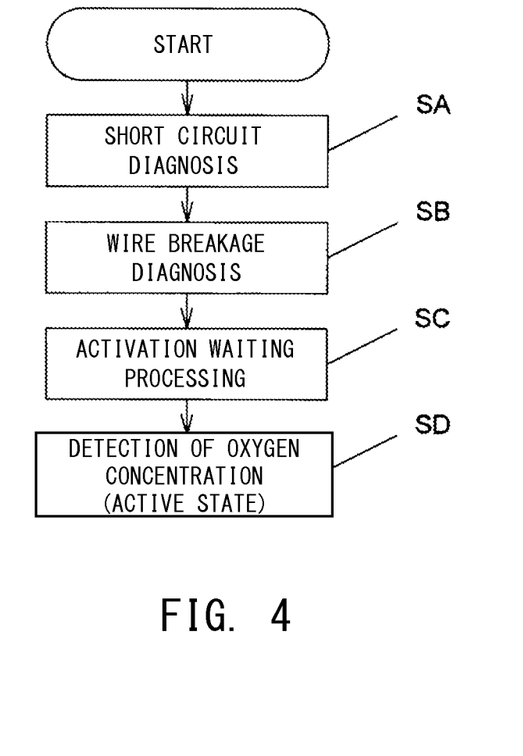
FIG. 4 is a flowchart showing the overall processing of the gas sensor system according to the embodiment.

FIG. 4 is a flowchart showing the overall processing of the gas sensor system 1. As shown in FIG. 4, when the gas sensor system 1 is started, the system 1 first performs the diagnosis of a short circuit anomaly (step SA). Subsequently, the system 1 performs the diagnosis of a wire breakage anomaly, including the start of supply of electric current to the heater section 80 (step SB). After performing the processing of waiting for activation (step SC), the system proceeds to the processing of detecting the oxygen concentration in an activated state (step SD).

The diagnosis of a short circuit anomaly of the gas sensor 2 (step SA of FIG. 4) will not be described herein. The diagnosis of a wire breakage anomaly of the gas sensor 2 (step SB of FIG. 4) performed by the sensor control section 40 will be described with reference to the flowcharts of FIGS. 5 and 6 showing the processing operation of the processor 30 as well as FIG. 2.

Figure 5:
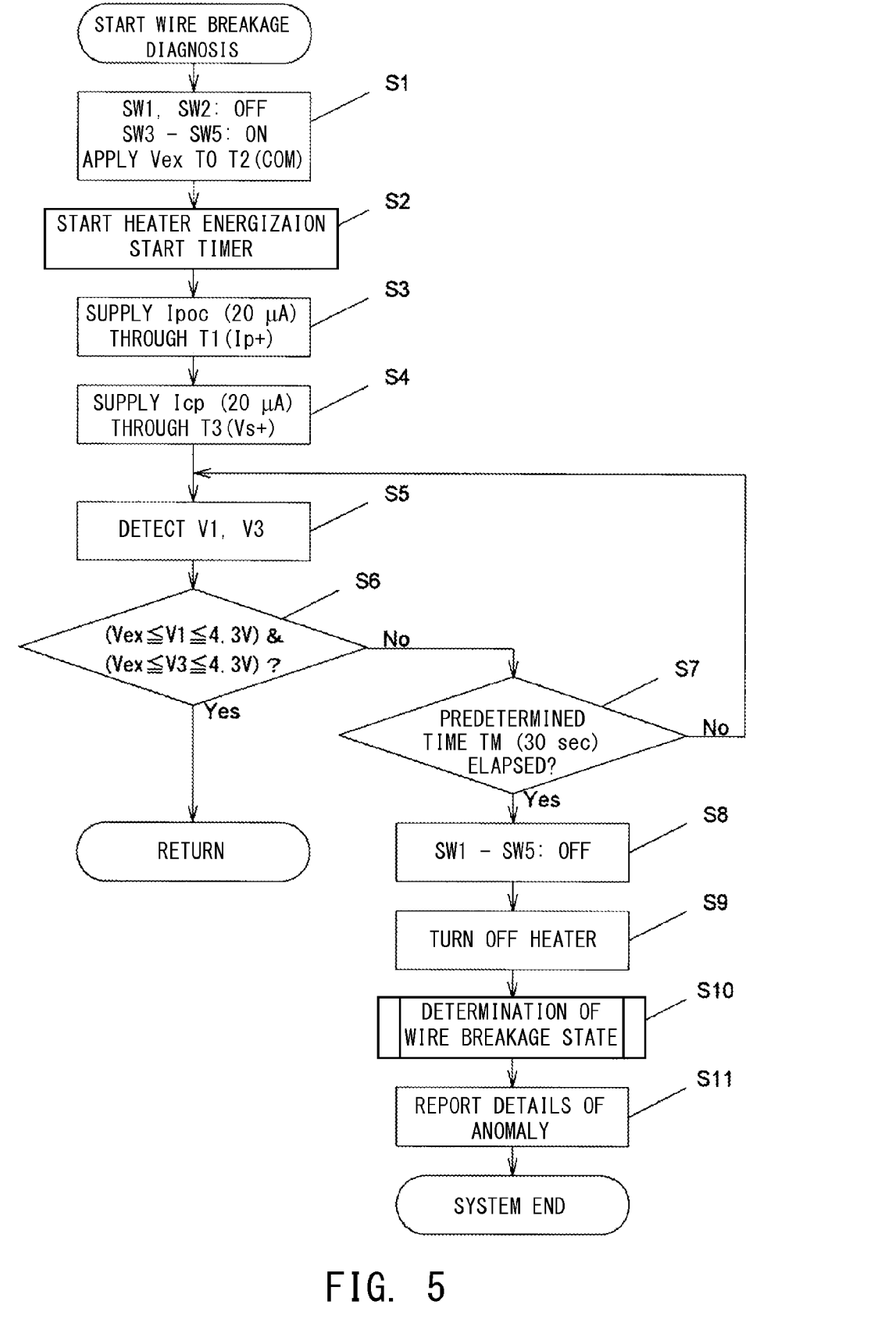
FIG. 5 is a flowchart showing a processing operation of a digital signal processor of the gas sensor system according to the embodiment at the time when the processor diagnoses a wire breakage anomaly.
Figure 6:
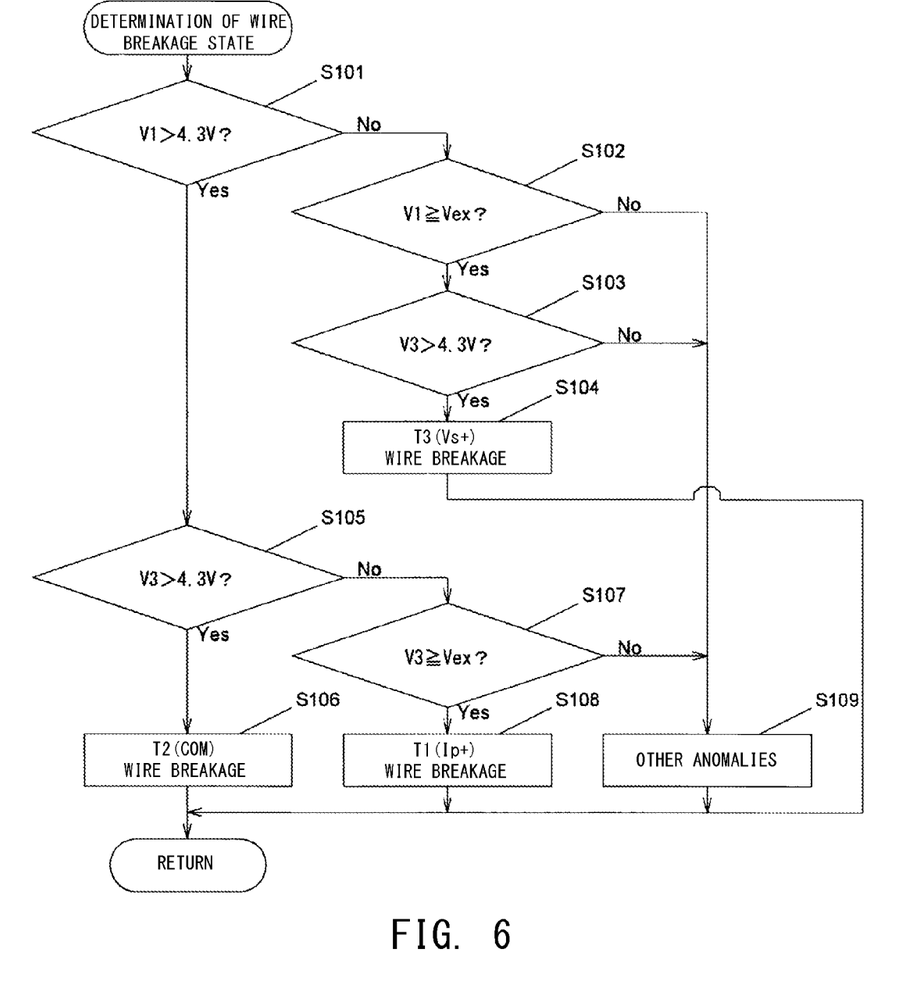
FIG. 6 is a flowchart showing operation of a digital signal processor of the gas sensor system according to the embodiment which executes a wire breakage state determination routine.

As shown in FIG. 5, in the case where the diagnosis of short circuit anomaly (step SA of FIG. 4) ends and no short circuit anomaly is present, the processor 30 starts the diagnosis of a wire breakage anomaly (step SB of FIG. 4), and proceeds to step S1.

In step S1, the processor 30 turns off the first switch SW1 and the second switch SW2, and turns on the third switch SW3 through the fifth switch SW5. As a result of the fourth switch SW4 being turned on, a reference potential Vref of +2.5 V is applied from the operational amplifier 44 to the second terminal T2 as an examination potential Vex (the examination potential Vex=+2.5 V (=the reference potential Vref)).

Subsequently, in step S2, the processor 30 starts the supply of electric current to the heater section 80 so as to start the heating (raising the temperature) of the gas sensor 2. Simultaneously, the processor 30 starts a timer for measuring time. Notably, even in the case where the gas sensor 2 has already been activated, for example, in the case of a hot restart in which the system 1 is restarted when the temperature of the gas sensor 2 is high, the diagnosis of a wire breakage anomaly is possible, and the following processing is performed as is.

Subsequently, in step S3, the processor 30 supplies a very small first examination current Ipoc (=20 μA), which is different from the pump current Ip, from the current DAC 47 to the oxygen pump cell 14 through the first terminal T1.

Further, in step S4 subsequent thereto, the processor 30 supplies a second examination current Icp (=20 μA), whose magnitude is the same as the above-mentioned constant minute current Icp, from the current DAC 48 to the oxygen concentration detection cell 24 through the third terminal T3 (the second examination current Icp=the minute current Icp). Notably, the above-mentioned first examination current Ipoc is set to have the same magnitude as the second examination current Icp (=the minute current Icp).

Next, in step S5, the processor 30 detects the first terminal potential V1 and the third terminal potential V3 using the A/D converters 41 and 43 during activation of the gas sensor 2.

Subsequently, in step S6, the processor 30 determines whether or not the first terminal potential V1 detected in step S5 falls within a first range which ranges from the examination potential Vex (=+2.5 V) to +4.3 V (=a first threshold potential V1$th$) lower than the maximum output voltage V1max (=+5 V) of the current DAC 47 (the first range: Vex≤V1≤+4.3 V). The processor 30 also determines whether or not the third terminal potential V3 detected in step S5 falls within a second range which ranges from the examination potential Vex (=+2.5 V) to +4.3 V (=a second threshold potential V3$th$) lower than the maximum output voltage V3max (=+5 V) of the current DAC 48 (the second range: Vex≤V3≤+4.3 V).

The fact that the first terminal potential V1 falls within the above-mentioned first range (Vex≤V1≤+4.3 V) shows that none of the first wiring line L1 through the third wiring line L3 has a wire breakage anomaly. In addition, this condition shows that, in a state in which the oxygen pump cell 14 exhibits oxygen ion conductivity and has a lowered internal resistance, the first terminal potential V1 becomes lower than the maximum output voltage V1max (=+5 V) of the current DAC 47 and becomes equal to a potential which is the sum of the examination potential Vex, a voltage drop generated as a result of the supply of the first examination current Ipoc to the internal resistor of the oxygen pump cell 14, and an electromotive force generated by the oxygen pump cell 14.

Similarly, the fact that the third terminal potential V3 falls within the above-mentioned second range (Vex≤V3≤+4.3 V)

shows that no wiring line has a wire breakage anomaly. In addition, this condition shows that, in a state in which the oxygen concentration detection cell 24 exhibits oxygen ion conductivity and has a lowered internal resistance, the third terminal potential V3 becomes lower than the maximum output voltage V3max (=+5 V) of the current DAC 48 and becomes equal to a potential which is the sum of the examination potential Vex, a voltage drop generated as a result of the supply of the second examination current Icp to the internal resistor of the oxygen concentration detection cell 24, and an electromotive force generated in the oxygen concentration detection cell 24.

Therefore, in the case where the first terminal potential V1 falls within the first range and the third terminal potential V3 falls within the second range (the result of the determination in step S6 is "Yes"), the processor 30 determines that the gas sensor 2 has no wire breakage anomaly, and proceeds to the activation waiting processing (step SC of FIG. 4).

Meanwhile, in the case where the first terminal potential V1 falls outside the first range and/or the third terminal potential V3 falls outside the second range (the result of the determination in step S6 is "No"), the processor 30 proceeds to step S7.

In step S7, the processor 30 judges whether or not a predetermined time TM (in the present embodiment, TM=30 seconds) has elapsed after the start of the supply of electric current to the heater section 80 in step S2 for heating the gas sensor 2. In the case where the predetermined time TM has not yet elapsed (No), the processor 30 returns to step S5 and repeats steps S5 to S7.

In the case where the predetermined time TM has elapsed ("Yes" in step S7) without the result of the determination in step S6 being "Yes," the processor 30 determines that the gas sensor 2 has a wire breakage anomaly, and proceeds to step S8.

The processor 30 determines that the gas sensor 2 has a wire breakage anomaly because of the following reason. In the case where the gas sensor 2 has a wire breakage anomaly; i.e., one of the first wiring line L1 through the third wiring line L3 is broken, the first examination current Ipoc and/or the second examination current Icp does not flow. Therefore, the current DAC 47 and/or the current DAC 48 keeps outputting the maximum output voltage V1max, V3max, and the first terminal potential V1 and/or the third terminal potential V3 becomes equal to the maximum output voltage V1max, V3max.

In step S8, the processor 30 turns off all of the first switch SW1 through the fifth switch SW5. Subsequently, the processor 30 proceeds to step S9, and cuts off the supply of electric current to the heater section 80.

Further, the processor 30 proceeds to step S10, and executes a wire breakage state determination routine (which will be described next) shown in FIG. 6. Notably, in this wire breakage state determination routine, the processor 30 determines the location of the wire breakage anomaly using the newest first and third terminal potentials V1 and V3 detected in step S5.

Upon completing execution of the wire breakage state determination routine, in step S11, the processor 30 reports the details of the anomaly (the result of determination of the wire breakage state) to the ECU 100. After that, the processing of the processor 30 is ended (system end) without proceeding to the activation wait processing (step SC of FIG. 4).

Next, the wire breakage state determination routine in step S10 will be described with reference to FIG. 6.

In this wire breakage state determination routine, in step S101, the processor 30 first determines whether or not the first terminal potential V1 is higher than +4.3 V (=the first threshold potential V1th). In the case where the first terminal potential V1 is higher than +4.3 V (Yes), the processor 30 proceeds to step S105, and in the other case; namely, in the case where the first terminal potential V1 is equal to or lower than +4.3 V (No), the processor 30 proceeds to step S102.

In step S102, the processor 30 determines whether or not the first terminal potential V1 is equal to or higher than the examination potential Vex. In the case where the first terminal potential V1 is equal to or higher than the examination potential Vex (Yes), the processor 30 proceeds to step S103, and in the other case; namely, in the case where the first terminal potential V1 is lower than the examination potential Vex (No), the processor 30 proceeds to step S109.

In step S103, the processor 30 determines whether or not the third terminal potential V3 is higher than +4.3 V (=the second threshold potential V3th). In the case where the third terminal potential V3 is higher than +4.3 V (Yes), the processor 30 proceeds to step S104, and in the other case; namely, in the case where the third terminal potential V3 is equal to or lower than +4.3 V (No), the processor 30 proceeds to step S109.

Meanwhile, in step S105, the processor 30 determines whether or not the third terminal potential V3 is higher than +4.3 V (=the second threshold potential V3th). In the case where the third terminal potential V3 is higher than +4.3 V (Yes), the processor 30 proceeds to step S106, and in the other case; namely, in the case where the third terminal potential V3 is equal to or lower than +4.3 V (No), the processor 30 proceeds to step S107.

In step S107, the processor 30 further determines whether or not the third terminal potential V3 is equal to or higher than the examination potential Vex. In the case where the third terminal potential V3 is equal to or higher than the examination potential Vex (Yes), the processor 30 proceeds to step S108, and in the other case; namely, in the case where the third terminal potential V3 is lower than the examination potential Vex (No), the processor 30 proceeds to step S109.

In the case where the processor 30 determined by the above-described processing that the first terminal potential V1 falls within the first range ranging from the examination potential Vex to +4.3 V (=the first threshold potential V1th) (Vex □V1 □+4.3 V) and the third terminal potential V3 is higher than +4.3 V (=the second threshold potential V3th) (V3>+4.3 V), the processor 30 proceeds to step S104. In step S104, the processor 30 determines that the third wiring line L3 connected to the third terminal T3 is broken (third wire breakage state), and determines the details of the anomaly to be reported to the ECU 100.

The processor 30 is able to make such a determination because of the following reason. In the third wire breakage state, since the second examination current Icp does not flow to the oxygen concentration detection cell 24 through the third terminal T3, the current DAC 48 keeps outputting the maximum output voltage V3max.

Meanwhile, in the case where the processor 30 determined by the above-described processing that the third terminal potential V3 falls within the second range ranging from the examination potential Vex to +4.3 V (=the second threshold potential V3th) (Vex≤V3≤+4.3 V) and the first terminal potential V1 is higher than +4.3 V (=the first threshold potential V1th) (V1>+4.3 V), the processor 30 proceeds to step S108. In step S108, the processor 30 determines that the first wiring line L1 connected to the first terminal T1 is broken (first wire breakage state) (determines the details of the anomaly).

The processor 30 is able to make such a determination because of the following reason. In the first wire breakage state, since the first examination current Ipoc does not flow to the oxygen pump cell 14 through the first terminal T1, the current DAC 47 keeps outputting the maximum output voltage V1max.

In the case where the first terminal potential V1 is higher than +4.3 V (=the first threshold potential V1$th$) (V1>+4.3 V) and the third terminal potential V3 is higher than +4.3 V (=the second threshold potential V3$th$) (V3>+4.3 V), the processor 30 proceeds to step S106. In step S106, the processor 30 determines that the second wiring line L2 connected to the second terminal T2 is broken (second wire breakage state) (determines the details of the anomaly).

The processor 30 is able to make such a determination because of the following reason. In the second wire breakage state, since none of the first examination current Ipoc and the second examination current Icp flows, the current DACs 47 and 48 keep outputting the maximum output voltages V1max and V3max.

In cases other than the above-described three cases, the processor 30 proceeds to step S109 and determines that the anomaly is one of other types of anomalies (determines the details of the anomaly).

After that, in each case where the processor 30 proceeds to step S104, or where the processor 30 proceeds to step S106, or where the processor 30 proceeds to step S108, or where the processor 30 proceeds to step S109, the processor 30 ends the wire breakage state determination routine, and proceeds to step S11 of FIG. 5 so as to report the details of the anomaly (the result of the determination of the wire breakage state) to the ECU 100.

Thus, by the wire breakage state determination routine of FIG. 6, the three wire breakage states (the first wire breakage state, the second wire breakage state, and the third wire breakage state) and other types of anomalies can be determined based on the first terminal potential V1 and the third terminal potential V3.

In the present embodiment, of the elements of the sensor control section 40, the A/D converter 41 which detects the first terminal potential V1 corresponds to the first terminal potential detection circuit, and the A/D converter 43 which detects the third terminal potential V3 corresponds to the third terminal potential detection circuit. The operational amplifier 44 corresponds to the examination potential circuit and the reference potential circuit, and the fourth switch SW4 corresponds to the reference potential switch. The current DAC 47 corresponds to the first constant current circuit and the pump current output circuit, and the third switch SW3 corresponds to the pump current switch. The constant minute current Icp supplied to the oxygen concentration detection cell 24 corresponds to the constant current, and the current DAC 48 corresponds to the second constant current circuit and the constant current output circuit. The fifth switch SW5 corresponds to the detection cell current switch.

In the present embodiment, the processor 30 which performs step S5 corresponds to the terminal potential detection means. The processor 30 which performs steps S6, S7, and S10 corresponds to the wire breakage diagnosis means. The processor 30 which performs steps S6 and S7 corresponds to the wire breakage absence determination means, and the processor 30 which performs step S10 corresponds to the wire breakage state determination means. The processor 30 which performs step S8 corresponds to the first cutoff means, the second cutoff means, and the third cutoff means.

In the gas sensor system 1 of the present embodiment, the second terminal T2 is brought to the examination potential Vex (=+2.5 V) before the gas sensor 2 detects the oxygen concentration of the exhaust gas EG in an activated state (specifically, during activation of the gas sensor 2 and before the activation waiting processing). Further, the first examination current Ipoc (=20 µA) is supplied to the oxygen pump cell 14 through the first terminal T1, the second examination current Icp (=20 µA) is supplied to the oxygen concentration detection cell 24 through the third terminal T3, and the first terminal potential V1 and the third terminal potential V3 are detected.

By virtue of such an operation, not only in the case where the gas sensor 2 has already been activated but also during activation, when the oxygen pump cell 14 and the oxygen concentration detection cell 24 exhibit oxygen ion conductivity and a lower internal resistance, the first terminal potential V1 and the third terminal potential V3 assume different values depending on whether or not each terminal has a wire breakage anomaly.

In view of the above, in the gas sensor system 1, the first terminal potential V1 and the third terminal potential V3 are detected in the above-described state, and, based on these potentials, the presence/absence of a wire breakage anomaly and the location of wire breakage anomaly are determined, through diagnosis, for the first terminal T1, the second terminal T2, and the third terminal T3.

As a result, in the gas sensor system 1, the presence/absence of a wire breakage anomaly and location of wire breakage anomaly can be properly determined through diagnosis not only after activation but also in the middle of activating the gas sensor 2.

In the gas sensor system 1 of the present embodiment, the wire breakage diagnosis means (steps S6, S7, and S10) determines the wire breakage absence state and the three wire breakage states based on the first terminal potential and the third terminal potential. Therefore, when a wire breakage anomaly has occurred, its location can be properly determined (step S10) and can be reported to the ECU 100 (step S11).

In the gas sensor system 1 of the present embodiment, the wire breakage absence determination means (steps S6 and S7) of a wire breakage diagnosis means determines that the gas sensor 2 is in the wire breakage absence state when the first terminal potential V1 falls within the first range and the third terminal potential V3 falls within the second range. As a result, it is possible to properly determine whether or not the gas sensor 2 is in the wire breakage absence state.

In the gas sensor system 1 of the present embodiment, when the wire breakage absence determination means (steps S6 and S7) determines that the gas sensor 2 is not in the wire breakage absence state (namely, when the gas sensor 2 has a wire breakage anomaly), the wire breakage state determination means (step S10) determines whether the wire breakage state is the first wire breakage state, the second wire breakage state, or the third wire breakage state (i.e., the location of the wire breakage anomaly).

In the wire breakage state determination means (step S10; namely, the wire breakage state determination routine shown in FIG. 6), the three wire breakage states can be properly determined based on the first terminal potential V1 and the third terminal potential V3 (steps S104, S106, and S108).

In the gas sensor system 1 of the present embodiment, the current DAC 48 has two functions; i.e., functions as a second constant current circuit for outputting the second examination current Icp and functions as a constant current output circuit for outputting the minute current Icp (the constant current). Therefore, when the diagnosis of wire breakage anomaly is performed, the current DAC 48 functioning as the constant current output circuit outputs the second examination current Icp. Accordingly, it is unnecessary to provide a dedicated circuit for supplying the second examination current Icp. Further, in the present embodiment, since the magnitude of the second examination current Icp is rendered equal to that of the minute current Icp (the second examination current Icp=the minute current Icp), the current DAC 48 (the constant current output circuit) is merely required to output a fixed current.

In the gas sensor system 1 of the present embodiment, the current DAC 47 has two functions; i.e., functions as a first constant current circuit for outputting the first examination current Ipoc and functions as a pump current output circuit for outputting the pump current Ip. Therefore, when a diagnosis of a wire breakage anomaly is performed, instead of the pump current Ip, the first examination current Ipoc can be output from the current DAC 47 functioning as the pump current output circuit. Accordingly, it is unnecessary to provide a dedicated circuit for supplying the first examination current Ipoc.

In the gas sensor system 1 of the present embodiment, in the case where the system 1 determines that a wire breakage anomaly is present, the system cuts off the first examination current Ipoc and the pump current Ip supplied to the oxygen pump cell 14 and the second examination current Icp and the minute current Icp (the constant current) supplied to the oxygen concentration detection cell 24 (step S8). Therefore, it is possible to prevent blackening of the oxygen pump cell 14 and the oxygen concentration detection cell 24, which would otherwise occur when the pump current Ip and the minute current Icp are supplied in a state in which the wire breakage anomaly continues.

In the gas sensor system 1 of the present embodiment, the operational amplifier 44, which functions as an examination potential circuit for applying the examination potential Vex, also functions as a reference potential circuit for applying the reference potential Vref after the gas sensor 2 is activated (the examination potential Vex=the reference potential Vref=+2.5 V). Therefore, it is unnecessary to provide a dedicated examination potential circuit for the diagnosis of a wire breakage anomaly.

In the gas sensor system 1 of the present embodiment, in the case where the system 1 determines that a wire breakage anomaly is present, the system 1 cuts off application of the reference potential Vref (=the examination potential Vex) (step S8). Therefore, it is possible to prevent blackening of the oxygen pump cell 14 and the oxygen concentration detection cell 24, which would otherwise occur when the reference potential Vref (=the examination potential Vex) is applied in a state in which the wire breakage anomaly continues.

The invention has been described in detail with reference to the above embodiment. However, the invention should not be construed as being limited thereto. It should further be apparent to those skilled in the art that various changes in form and detail of the invention as shown and described above may be made. It is intended that such changes be included within the spirit and scope of the claims appended hereto.

For example, in the embodiment, the gas sensor 2 is an air-fuel-ratio sensor (full-range air-fuel-ratio sensor) which detects the concentration of oxygen (air-fuel ratio) within an exhaust gas EG. However, the "gas sensor" is not limited to an air-fuel-ratio sensor, and may be an NOx sensor for detecting the concentration of nitrogen oxide (NOx).

Also, the sensor control section 40 may be incorporated into the ECU 100.

In the gas sensor system 1 of the embodiment, the sensor control section 40 is constituted by an ASIC including the digital signal processor 30, and the PID control of the pump current Ip is performed by a digital scheme.

However, the present invention can be applied to a gas sensor system which has a sensor control section composed of an ASIC including an analog PID circuit and a separately provided microprocessor and in which the PID control is performed by an analog scheme.

This application is based on Japanese Patent Application No. 2014-203301 filed Oct. 1, 2014, incorporated herein by reference in its entirety.

What is claimed is:

1. A gas sensor system comprising:
a gas sensor having an oxygen pump cell electrically communicating with a first terminal and a second terminal, and an oxygen concentration detection cell electrically communicating with the second terminal and a third terminal, the gas sensor detecting the concentration of a specific gas contained in a gas under measurement; and
a sensor control section which includes a first terminal potential detection circuit for detecting a first terminal potential of the first terminal and a third terminal potential detection circuit for detecting a third terminal potential of the third terminal and which controls the gas sensor through the first terminal, the second terminal, and the third terminal, wherein
the sensor control section includes:
an examination potential circuit which brings the second terminal to a predetermined examination potential;
a first constant current circuit which supplies a predetermined first examination current to the oxygen pump cell through the first terminal;
a second constant current circuit which supplies a predetermined second examination current to the oxygen concentration detection cell through the third terminal;
terminal potential detection means for detecting the first terminal potential and the third terminal potential using the first terminal potential detection circuit and the third terminal potential detection circuit, before the gas sensor detects in an activated state the concentration of the specific gas contained in the gas under measurement, and in a state in which the second terminal is brought to the examination potential by the examination potential circuit, the first examination current is supplied from the first constant current circuit to the oxygen pump cell through the first terminal, and the second examination current is supplied from the second constant current circuit to the oxygen concentration detection cell through the third terminal; and
wire breakage diagnosis means for determining whether or not the gas sensor has a wire breakage anomaly and a location where the wire breakage anomaly has occurred based on the detected first terminal potential and the detected third terminal potential, and wherein
the first examination current and the second examination current are low enough that the first terminal potential and the second terminal potential become lower than a maximum output voltage of the first constant current circuit and the second constant current circuit when the oxygen pump cell and the oxygen concentration detection cell exhibit an internal resistance of from greater than or equal to the internal resistance of the oxygen pump cell and the oxygen concentration detection cell when the sensor is in an activated state to an internal resistance that is lower than the internal resistance when the oxygen pump cell and the oxygen concentration detection cell first exhibit oxygen ion conductivity upon heating the sensor.

2. The gas sensor system as claimed in claim 1, wherein the wire breakage diagnosis means determines, based on the first terminal potential and the third terminal potential,
   a wire breakage absence state in which none of a first wiring line connecting the oxygen pump cell to the first terminal, a second wiring line connecting the oxygen pump cell and the oxygen concentration detection cell to the second terminal, and a third wiring line connecting the oxygen concentration detection cell to the third terminal is broken,
   a first wire breakage state in which the first wiring line is broken,
   a second wire breakage state in which the second wiring line is broken, and
   a third wire breakage state in which the third wiring line is broken.

3. The gas sensor system as claimed in claim 2, wherein the wire breakage diagnosis means includes wire breakage absence determination means which determines that the gas sensor is in the wire breakage absence state when the first terminal potential falls within a first range ranging from the examination potential to a first threshold potential lower than the maximum output voltage of the first constant current circuit, and the third terminal potential falls within a second range ranging from the examination potential to a second threshold potential lower than the maximum output voltage of the second constant current circuit.

4. The gas sensor system as claimed in claim 3, wherein the wire breakage diagnosis means includes wire breakage state determination means, operable when the wire breakage absence determination means determines that the gas sensor is not in the wire breakage absence state, for determining based on the first terminal potential and the third terminal potential, whether the gas sensor is in the first wire breakage state, the second wire breakage state, or the third wire breakage state.

5. The gas sensor system as claimed in claim 4, wherein
   the wire breakage state determination means determines that the gas sensor is in the first wire breakage state when the third terminal potential falls within the second range and the first terminal potential is higher than the first range,
   the wire breakage state determination means determines that the gas sensor is in the second wire breakage state when the first terminal potential is higher than the first range and the third terminal potential is higher than the second range, and
   the wire breakage state determination means determines that the gas sensor is in the third wire breakage state when the first terminal potential falls within the first range and the third terminal potential is higher than the second range.

6. The gas sensor system as claimed in claim 1, wherein
   the gas sensor internally has a measurement chamber into which the gas under measurement is introduced and a reference oxygen chamber in which a reference oxygen atmosphere is generated;
   the oxygen concentration detection cell has a first detection electrode facing the reference oxygen chamber and electrically communicating with the third terminal and a second detection electrode exposed to the measurement chamber and electrically communicating with the second terminal; and
   the second constant current circuit comprises a constant current output circuit which supplies a constant current to the oxygen concentration detection cell through the third terminal so as to pump oxygen into the reference oxygen chamber.

7. The gas sensor system as claimed in claim 6, wherein the sensor control section includes:
   a detection cell current switch for turning on and turning off supply of the second examination current and the constant current from the constant current output circuit to the oxygen concentration detection cell through the third terminal, and
   first cutoff means for turning off the detection cell current switch when the wire breakage diagnosis means determines that a wire breakage anomaly is present.

8. The gas sensor system as claimed in claim 1, wherein
   the gas sensor internally has a measurement chamber into which the gas under measurement is introduced;
   the oxygen pump cell has a first pump electrode disposed outside the measurement chamber and electrically communicating with the first terminal and a second pump electrode exposed to the measurement chamber and electrically communicating with the second terminal; and
   the first constant current circuit comprises a pump current output circuit which supplies a pump current to the oxygen pump cell through the first terminal so as to pump oxygen out of or into the measurement chamber.

9. The gas sensor system as claimed in claim 8, wherein the sensor control section includes:
   a pump current switch for turning on and turning off supply of the first examination current and the pump current from the pump current output circuit to the oxygen pump cell through the first terminal, and
   second cutoff means for turning off the pump current switch when the wire breakage diagnosis means determines that a wire breakage anomaly is present.

10. The gas sensor system as claimed in claim 1, wherein the examination potential circuit comprises a reference potential circuit which applies a reference potential to the second terminal after the gas sensor is activated.

11. The gas sensor system as claimed in claim 10, wherein the sensor control section includes:
   a reference potential switch for turning on and turning off application of the examination potential and the reference potential from the reference potential circuit to the second terminal, and
   third cutoff means for turning off the reference potential switch when the wire breakage diagnosis means determines that a wire breakage anomaly is present.

* * * * *